(12) United States Patent
Patnode

(10) Patent No.: US 8,481,006 B2
(45) Date of Patent: Jul. 9, 2013

(54) MELT FORMULA

(75) Inventor: Diahne Patnode, Chandler, AZ (US)

(73) Assignee: New Sunshine, LLC, Indianapolis, IN (US)

( * ) Notice: Subject to any disclaimer, the term of this patent is extended or adjusted under 35 U.S.C. 154(b) by 892 days.

(21) Appl. No.: 12/149,058

(22) Filed: Apr. 25, 2008

(65) Prior Publication Data
US 2009/0269290 A1 Oct. 29, 2009

(51) Int. Cl.
*A61K 8/18* (2006.01)
*A61Q 17/04* (2006.01)

(52) U.S. Cl.
USPC ............ 424/59; 424/63; 424/64; 424/60; 424/400; 424/401

(58) Field of Classification Search
USPC .................. 424/60, 63, 64, 400, 401
See application file for complete search history.

(56) References Cited

U.S. PATENT DOCUMENTS

| | | | |
|---|---|---|---|
| 3,937,808 A * | 2/1976 | Strobel .................. 424/59 |
| 3,957,969 A * | 5/1976 | Fujiyama et al. ........ 424/64 |
| 4,714,609 A | 12/1987 | Carden |
| 5,747,049 A | 5/1998 | Tominaga |
| 5,766,575 A | 6/1998 | Crotty |
| 5,985,177 A | 11/1999 | Yoshida et al. |
| 6,077,520 A | 6/2000 | Tominaga |
| 6,280,712 B1 | 8/2001 | Ansmann et al. |
| 6,328,892 B1 | 12/2001 | Jones |
| 6,342,208 B1 | 1/2002 | Hyldgaard et al. |
| 6,409,996 B1 | 6/2002 | Plaschke |
| 6,416,768 B1 | 7/2002 | Ravaux et al. |
| 6,432,441 B1 | 8/2002 | Bealin-Kelly et al. |
| 6,471,972 B1 | 10/2002 | Bonte et al. |
| 6,602,492 B2 | 8/2003 | Iwasaki |
| 6,630,163 B1 | 10/2003 | Murad |
| 6,645,510 B1 | 11/2003 | Coury et al. |
| 6,673,844 B2 | 1/2004 | Kumamoto et al. |
| 6,699,463 B2 | 3/2004 | Chaudhuri |
| 6,780,443 B1 | 8/2004 | Nakatsu et al. |
| 6,831,191 B2 | 12/2004 | Chaudhuri |
| 6,858,217 B2 | 2/2005 | Kerschner et al. |
| 6,863,897 B2 | 3/2005 | Love et al. |
| 6,869,598 B2 | 3/2005 | Love et al. |
| 6,890,567 B2 | 5/2005 | Nakatsu et al. |
| 6,899,901 B2 * | 5/2005 | Nakatsu et al. ............ 424/725 |
| 6,984,390 B2 | 1/2006 | Sakuta |
| 7,001,592 B1 | 2/2006 | Traynor et al. |
| 7,008,628 B2 | 3/2006 | Ron et al. |
| 7,214,382 B2 | 5/2007 | Shefer et al. |
| 7,226,582 B2 | 6/2007 | Traynor et al. |
| 2003/0068286 A1 | 4/2003 | Stroud |
| 2003/0215522 A1 * | 11/2003 | Johnson et al. ............. 424/642 |
| 2004/0076652 A1 | 4/2004 | Paspaleeva-Kuhn et al. |
| 2004/0220087 A1 * | 11/2004 | Bar-Or ........................ 514/7 |
| 2005/0048008 A1 | 3/2005 | Gupta |
| 2005/0118124 A1 | 6/2005 | Reinhart et al. |
| 2005/0129633 A1 | 6/2005 | Lin |
| 2005/0175556 A1 * | 8/2005 | Gupta ......................... 424/59 |
| 2005/0187164 A1 | 8/2005 | Pinel |
| 2005/0239669 A1 | 10/2005 | Krzysik et al. |
| 2005/0255060 A1 | 11/2005 | Oblong et al. |
| 2006/0110415 A1 | 5/2006 | Gupta |
| 2006/0188457 A1 | 8/2006 | Traynor et al. |
| 2006/0188458 A1 | 8/2006 | Traynor et al. |
| 2006/0198800 A1 | 9/2006 | Dilallo et al. |
| 2006/0222619 A1 * | 10/2006 | Perrier et al. ................. 424/74 |
| 2007/0110778 A1 | 5/2007 | Anderson |
| 2007/0154439 A1 | 7/2007 | Dorf |
| 2007/0196291 A1 | 8/2007 | Sakuta |

* cited by examiner

*Primary Examiner* — Ernst Arnold
*Assistant Examiner* — Hong Yu
(74) *Attorney, Agent, or Firm* — Kramer & Amado, P.C.

(57) ABSTRACT

A topical composition comprises a vehicle, said vehicle including an emulsion or dispersion of water in an amount of from 50% by weight to 93% by weight; and a non-aqueous discontinuous phase in an amount of from 50% by weight to 7% by weight; at least one of a bronzer, a tanning accelerator, or a mixture thereof; and from 0.01% by weight to 5% by weight of a warming agent, based on the total weight of the composition. The warming agent comprises at least one alkyl ether of vanillyl alcohol at least one N-alkyl amide of vanillic acid; and is present in an amount effective to produce a prolonged warming sensation when applied to a user's skin. The composition is transparent to UV radiation. The composition is used for indoor tanning.

14 Claims, No Drawings

MELT FORMULA

BACKGROUND OF THE INVENTION

1. Field of the Invention

Various exemplary embodiments of the invention relate generally to a cosmetic formulation for indoor tanning, and more particularly to a formulation for indoor tanning containing a sensory agent. Various exemplary embodiments relate to methods of tanning using such a formulation.

2. Summary of Related Art

Indoor tanning equipment typically employs ultraviolet lights positioned beneath and above a planar surface made out of materials transparent to ultraviolet radiation such as acrylic Plexiglas. This tanning equipment has become increasingly popular for acquiring a quick and safe tan. Many sensory experiences have been added to indoor tanning equipment such as fans, music, hydration, radiant heat and massage to name a few.

Sensate additives to tanning compositions have also been used. Currently marketed sensate additions to topical indoor tanning lotions include fragrances, cooling sensates and tingle sensates. Indoor tanning products of the prior art which produce a "warming" sensation typically use esters of nicotinic acid. Nicotinic esters have the negative effect of undesirably reddening the skin while producing a warming sensation which only lasts for a short period of time. Various exemplary embodiments of the current invention relate to a novel topically applied composition containing a "warming agent" as a sensate additive for use with indoor tanning equipment. The inventive compositions induce a warming, long lasting, non-reddening sensory experience without radiant heat or esters of nicotinic acid while utilizing indoor tanning equipment. The present invention can be utilized in conjunction with current types of fragrances, cooling sensate materials and tingling sensate materials available on the market.

Known "warming agents" often exhibit insufficient warming effects, and those having high warming effects are of short duration or, when used in a reduced amount, have insufficient warming effects or an insufficient duration of effect. The current invention of a topically applied "warming sensate" composition to be used in conjunction with the indoor tanning equipment during the tanning session has shown the sensory experience is a unique sensation to other currently marketed compositions intended for use during the tanning bed session and continues for several hours concluding the tanning session.

Various tanning compositions in the form of lotions or pills according to the prior art contain tanning accelerators. Many of these tanning accelerators include the amino acid tyrosine, which is alleged to stimulate and increase melanin formation, thereby accelerating the tanning process. These tanning accelerators are used in conjunction with UV exposure.

Cosmetic formulations which contain sensory agents which provide a tingling or warming sensation are known. Such agents may include any of a variety of ethers, esters and amides derived from vanillin. These vanillin derivatives provide a pleasant warming sensation to the skin when applied topically. In many such formulations, however, the warming sensation is short-lived.

However, many of these cosmetic or topical formulations contain colorant ingredients or active ingredients which interview with the passage of U.V. radiation. These colorants or active ingredients may prevent U.V. radiation from reaching the melanocytes in the skin by reflecting U.V. radiation or by absorbing U.V. radiation. This prevents the topical formulation from effectively allowing or promoting tanning. This problem would be solved by a preparation which is substantially transparent to U.V. radiation.

SUMMARY OF THE INVENTION

In light of the present need for improved cosmetic tanning compositions which offer a prolonged warming sensation while remaining substantially transparent to U.V. radiation, a brief summary of various exemplary embodiments is presented. Some simplifications and omission may be made in the following summary, which is intended to highlight and introduce some aspects of the various exemplary embodiments, but not to limit its scope. Detailed descriptions of a preferred exemplary embodiment adequate to allow those of ordinary skill in the art to make and use the invention concepts will follow in later sections.

Topical substances which are known to provide a sensation of warmth on application will be referred to as "warming agents". "Warming agents," for the purposes of this disclosure, are defined to include vanillyl alcohol alkyl ether derivatives, such as vanillyl ethyl ether, vanillyl butyl ether, vanillyl pentyl ether, and vanillyl hexyl ether, isovanillyl alcohol alkyl ethers, ethylvanillyl alcohol alkyl ethers. Amides of vanillic acid, such as nonyl vanillamide, may also be used as warming agents. These warming agents are added either as such or in the form of a fragrance composition to various products to produce a warming effect.

The current invention is a topically applied composition that includes a "warming agent" either in conjunction with other botanical extracts known to increase microcirculation or without. This is a unique sensate experience not from the sophistication of the tanning bed equipment, but from a topically applied composition to be used in conjunction with the indoor tanning equipment during the tanning session. The sensory experience continues for several hours after the tanning session.

Various exemplary embodiments of the present invention relate to a composition for use in indoor tanning equipment that can be spread topically on the skin; will not interfere with the passage of ultraviolet radiation of the wavelength required for effective tanning; and will not contaminate the surface of the equipment.

One embodiment of the invention relates to a topical composition comprising a vehicle, said vehicle being an emulsion or dispersion of water in an amount of from 50% by weight to 93% by weight; and a non-aqueous discontinuous phase in an amount of from 50% by weight to 7% by weight; at least one of a bronzer, a tanning accelerator, or a mixture thereof; and from 0.01% by weight to 5% by weight of a warming agent, based on the total weight of the composition. The warming agent comprises at least one alkyl ether of vanillyl alcohol or at least one N-alkyl amide of vanillic acid; where the alkyl ether of vanillyl alcohol is present in an amount effective to produce a prolonged warming sensation when applied to a user's skin. The composition is transparent to UV radiation.

In a further embodiment of the invention, a topical composition comprises a vehicle, said vehicle being an emulsion or dispersion of water in an amount of from 50% by weight to 93% by weight; and a non-aqueous discontinuous phase in an amount of from 50% by weight to 7% by weight; at least one bronzer; and from 0.01% by weight to 5% by weight of a warming agent, based on the total weight of the composition. The bronzer is selected from the group consisting of black walnut extract, henna extract, kukui nut husk extract, and gymnema extract.

In an additional embodiment of the invention, a topical composition comprises a vehicle, said vehicle being an emulsion or dispersion of water in an amount of from 50% by weight to 93% by weight; and a non-aqueous discontinuous phase in an amount of from 50% by weight to 7% by weight; at least one tanning accelerator; and from 0.01% by weight to 5% by weight of a warming agent, based on the total weight of the composition. The tanning accelerator is selected from the group consisting of:

i) tyrosine, a tyrosine derivative, or a mixture thereof;
ii) α-melanocyte stimulating hormone, β-melanocyte stimulating hormone, γ-melanocyte stimulating hormone, or analogs thereof; or
iii) tyrosine or a tyrosine derivative in combination with α-melanocyte stimulating hormone, β-melanocyte stimulating hormone, γ-melanocyte stimulating hormone, or an analog thereof.

In a further embodiment, a method of indoor tanning is described. The method comprises a step of applying a topical composition to an exposed skin surface, where the topical composition comprises a vehicle including an emulsion or dispersion of water in an amount of from 50% by weight to 93% by weight; and a non-aqueous discontinuous phase in an amount of from 50% by weight to 7% by weight; and from 0.01% by weight to 5% by weight of a warming agent, based on the total weight of the composition. The warming agent comprises at least one alkyl ether of vanillyl alcohol or at least one N-alkyl amide of vanillic acid; where the warming agent is present in an amount effective to produce a prolonged warming sensation when applied to a user's skin. The composition is transparent to UV radiation. In a second step, the exposed skin surface is exposed to an indoor source of ultraviolet light.

In another embodiment, a method of making a topical tanning composition is described. The method comprises a step of mixing a nonaqueous phase and an aqueous phase to prepare a vehicle in the form of an emulsion or dispersion. The aqueous phase includes water in an amount of from 50% by weight to 93% by weight of the vehicle; and the nonaqueous phase is present in an amount of from 50% by weight to 7% by weight of the vehicle. In a second step, at least one of a bronzer, a tanning accelerator, or a mixture thereof is added to the nonaqueous phase prior to the mixing step; to the aqueous phase prior to the mixing step; or to the vehicle after the mixing step. Next, from 0.01% by weight to 5% by weight of a warming agent is added to the nonaqueous phase prior to the mixing step; to the aqueous phase prior to the mixing step; or to the vehicle after the mixing step, based on the total weight of the composition. The warming agent comprises at least one alkyl ether of vanillyl alcohol or at least one N-alkyl amide of vanillic acid; and is added in an amount effective to produce a prolonged warming sensation when applied to a user's skin.

BRIEF DESCRIPTION OF THE PREFERRED EMBODIMENTS

Although the various exemplary embodiments have been described in detail with particular reference to certain exemplary aspects thereof, it should be understood that the invention is capable of other different embodiments, and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only, and do not in any way limit the invention, which is defined only by the claims.

In light of the current need for cosmetic tanning formulations which give rise to a prolonged warming sensation upon application to the skin, various exemplary embodiments of the invention disclosed herein are directed to a topical composition for use with Indoor Tanning Equipment containing an aqueous continuous phase and a non-aqueous discontinuous phase. The tanning formulation, when applied, is substantially transparent to ultraviolet radiation.

The compositions described herein are generally formed as emulsions. Emulsions are generally formed from at least two liquid phases which are immiscible so that at least one of the phases is dispersed in fine form throughout the other phase(s). While emulsions are often formed by many components in complex relationships, they can be broadly classified as either oil-in-water or water-in-oil emulsions, depending on which of the phases comprises the dispersed inner phase and which is the continuous outer phase. In this context, an oil may be defined as any material immiscible with water and capable of forming an emulsion with water. Various agents are used to retard or inhibit the separation of emulsions into their constituent phases and these agents may determine the type of emulsion formed. Additionally, the nature of the emulsion can be reversed depending on the agent employed. The preferred embodiment of the composition is a stabilized oil-in-water ("o/w") emulsion.

Topical substances which are known to provide a sensation of warmth on application will be referred to as "warming agents". "Warming agents," for the purposes of this disclosure, are defined to include vanillyl alcohol alkyl ether derivatives, such as vanillyl ethyl ether, vanillyl butyl ether, vanillyl pentyl ether, and vanillyl hexyl ether, isovanillyl alcohol alkyl ethers, ethylvanillyl alcohol alkyl ethers. Amides of vanillic acid or its derivatives, such as nonyl vanillamide or 8-methyl-N-vanillyl-6-nonenamide, may also be used as warming agents. These warming agents are added either as such or in the form of a fragrance composition to various products to produce a warming effect. The warming agents may be added to an aqueous phase, which will then be combined with a nonaqueous phase to form an emulsion or dispersion. Alternatively, the warming agents may be added to a non-aqueous phase, which will then be combined with an aqueous phase to form an emulsion or dispersion. As a further alternative, a non-aqueous phase may be combined with an aqueous phase to form an emulsion or dispersion in the absence of a warming agent; the warming agent is then added to the emulsion or dispersion. Vanillyl ethers and amides cause a warming effect by stimulating circulation and enhancing blood flow. As a cardiovascular stimulant, vanillyl ethers and amides assist in lowering blood pressure. The warming properties of vanillyl ethers and amides are useful for people suffering from poor circulation to the hands and feet and other related conditions.

The nonaqueous phase contains at least one hydrophobic or water-repellant solvent, wax or oil. Suitable oils include cyclic and acyclic silicone oils, plant-derived triglycerides, such as peanut, soya bean, sunflower, sesame, coconut, olive and other vegetable oils; and. Suitable waxes include C12-C26 fatty alcohols; C12-C26 fatty acids; alkyl esters of C12-C26 fatty acids; C2-C5 linear or branched glycol diesters of C12-C26 fatty acids; C12-C26 fatty alcohol esters of carboxylic acids; beeswax; carnauba wax; and paraffin wax. When the nonaqueous and aqueous phases are combined, at least one emulsifier or surfactant is present. The emulsifier or surfactant may be anionic, cationic, nonionic, or zwitterionic. Mixtures of nonionic surfactants with either cationic or nonionic surfactants may also be used.

The anionic surfactants employed may be salts of fatty acids (for example alkaline salts or organic salts such as amine salts), the said fatty acids having, for example, from 12 to 18 carbon atoms and being able to have a double bond as in the case of oleic acid; alkaline salts or organic base salts of alkylsulfates and alkylsulfonates having 12 to 18 carbon atoms; alkylsulfosuccinic acids whose alkyl chain contains from 6 to 18 carbon atoms; anionic sphingolipids; and alkylphenylsulfonic acids whose alkyl chain contains from 6 to 18 carbon atoms. They may also be alkyl ether sulfates, in particular the sulfonation products of polyalkoxylated fatty alcohols and polyalkoxylated alkyl phenols in which the aliphatic chain contains from 6 to 20 carbon atoms and the polyalkoxylated chain from 1 to 30 oxyalkylene units, in particular oxyethylene, oxypropylene or oxybutylene. Also, C6-C26 monoalkyltartrates may be used as anionic surfactants.

The nonionic surfactants are principally polyalkoxylated and/or polyglycerolated surfactants. They are principally polyalkoxylated and/or polyglycerolated fatty acids or amides of fatty acids; polyalkoxylated and/or polyglycerolated fatty alcohols or alkylphenols; polyalkoxylated and/or polyglycerolated esters of fatty acids and polyols; polyalkoxylated and/or polyglycerolated 1,2- or 1,3-alkanediols or alkanediols; polyalkoxylated and/or polyglycerolated alkylethers of 1,2- or 1,3-alkanediols or alkanediols; C6-C26 dialkyl tartrates; and nonionic sphingolipids. For example, the fatty acids or alcohols, optionally unsaturated, have 12-24 carbon atoms, the alkyl chain of the alkylphenols has 6 to 16 carbon atoms, the alkanediols or alkanediols have from 9 to 24 carbon atoms, the alkyl of the alkylethers has from 4 to 20 carbon atoms, and the number of oxyalkylene units or of ($CH_2CHOHCH_2O$) units can range from 2 to 40. The polyalkoxylated nonionic derivatives are principally polyoxyethylenated, optionally polyoxypropylenated derivatives. Ethoxylated fatty acid esters of sorbitan, such as Polysorbate 20, may also be used as nonionic surfactants.

The cationic surfactants can be chosen from quaternary ammonium derivatives such as C6-C18 dialkyldimethylammonium salts; C6-C18 alkyltrimethylammonium salts; and C6-C18 alkyldimethylbenzylammonium salts. Quaternary phosphonium salts may also be used Polymeric thickeners such as polysaccharide starches or vegetable gums; proteins such as albumin, gelatin, hydrolyzed vegetable protein, or collagen; and polyacrylate or polyacrylamide thickeners may be added to the emulsion to increase the viscosity. Other thickeners can be polyols like sorbitol, xylitol, dextran and maltitol, or polymeric polyols like polydextrose or natural extracts like quillaia.

The aqueous phase is combined with the oil or wax, the surfactant, and the emulsifier, and mixed to produce a smooth and uniform cream or gel. Additional active agents are then added to the cream or gel. Various dermatologically acceptable fragrances and colorants may be added to the cream or gel. Antibacterial and antifungal agents such as triclosan may also be added.

Additional active components which are effective as tanning accelerators or melanin accelerators may be added to the lotion. In various exemplary embodiments, these tanning accelerators include tyrosine and/or derivatives thereof. Such derivatives include N-acetyl tyrosine, N-acetyl o-dihydroxymethylsilyltyrosine (Tyrosilane C®), N-caproyl tyrosine (Tyrostan®), glucose tyrosinate, 3,4-dihydroxyphenylalanine, and alkali metal salts thereof. The tyrosine-derived pigment melanin may also be added. Sulfate salts selected from the group consisting of magnesium sulfate, manganese sulfate, copper sulfate, zinc sulfate, and a combination thereof may also be used as tanning accelerators, alone or in combination with hydrolyzed algin. *Coelus Forskohlii* Extract and *Micrococcus* Lysate are effective as melanin accelerators. A wide variety of vegetable extracts may be used as melanin accelerators. Such extracts include citrus aurantium dulcis (orange) fruit extract, hydrolyzed citrus aurantium dulcis fruit extract, citrus aurantium dulcis peel extract, cocoa fruit extract, and vanilla planifolia fruit extract. Vegetable melanin is also effective as a melanin accelerator. Extracts of *Saccharomyces* yeasts fermented in the presence of magnesium, copper and/or zinc ions are effective as melanin accelerators.

Other tanning accelerators may also be added. For example, tanning accelerator peptides may be added. The tanning accelerator peptides may be selected from the group consisting of α-melanocyte stimulating hormone, β-melanocyte stimulating hormone, γ-melanocyte stimulating hormone and analogs thereof. The melanocyte-stimulating hormones (collectively referred to as MSH) are a class of peptide hormones. They stimulate the production and release of melanin (melanogenesis) by melanocytes in skin and hair. MSH is also produced by a subpopulation of neurons in the arcuate nucleus of the hypothalamus. MSH causes a darkening of skin pigmentation. Synthetic peptides which are structurally related to MSH, or which perform the same function as MSH, may be used to partially or completely replace MSH. An example of such a peptide is acetyl hexapeptide-1, commercially available as Melitane.

The cream or lotion may contain a wide variety of extracts of plants and microorganisms which act as bronzers. These bronzers are plant extracts which give a suntan-like color to skin. For example, black walnut leaf extracts and/or kukui nut husk extracts may be added to the formulation as bronzers; in addition to their cosmetic effect, these bronzers have additional health benefits. Walnut leaves contain astringent tannins which cross-link skin cells, making them impermeable to allergens and infectious microorganisms. Walnut leaves also contain antibacterial agents. Kukui oil assists the skin in maintaining its water barrier function, and is useful in the topical treatment of viral infections. Fruit, flower, and/or leaf extracts of henna and *Gymnema sylvestre* leaf extracts are other preferred bronzers. Other extracts useful as bronzers include *Musa Sapientum* (Banana) Fruit Extract, carrot seed oil, *Cucumis Melo* (Melon) Fruit Extract, mustard, black tea extract, chicory root extract, hibiscus extracts, wasabi extracts, red beet extracts, paprika extracts, red clover extracts, and vegetable melanin. Other bronzing agents which may be used include melanin, erythrulose, dihydroxyacetone, a mixture of erythrulose and dihydroxyacetone, and caramel color.

A variety of antioxidant extracts may also be added to the cream or lotion. These antioxidant extracts include *Ligustrum Lucidum* Fruit Extract, *Hypericum Perforatum* Flower, Leaf and Stem Extracts, *Phellodendron Amurense* Bark Extract, *Orobanche Rapum* Extract, *Helianthus Annuus* (Sunflower) Seed Extract, *Leontopodium Alpinum* Flower and Leaf Extracts, and *Bixa Orellana* Seed Extract.

Nucleotides such as adenosine monophosphate, adenosine triphosphate, and cyclic adenosine monophosphate, may also be added to the tanning formulation. Adenosine is a potent topical anti-inflammatory agent, acting at its four G-protein coupled receptors. Adenosine therefore may be useful in treating inflammation from excessive sun exposure.

The formulation may contain transdermally available vitamins, including vitamin A, vitamin C, and vitamin E. An analog of Vitamin A, Retinyl Palmitate Polypeptide, helps to reverse photo-damage to the skin from the sun. A useful form of vitamin C is L-ascorbic acid polypeptide complex, a water stable, soluble form of Vitamin C, which is able to penetrate the outer layers of the skin. On topical application, it enters the melanocyte cells in the skin. Vitamin E is used in the form of α-tocopheryl nicotinate. Soy proteins and/or amino acids may also be added to enhance protein formation in the skin. Vitamins and amino acids also enhance tanning by moisturizing the skin and contributing to a uniform tan color.

Other additives can include, depending on the use, glycols, sunscreen agents, humectants, preservatives, such as known parabens, emollients, occlusive agents, and esters. Depending on the use of the composition, the other additives may be dispersible in the oil or water phase. Preferably, the additives are incorporated in the appropriate phase before the oil mix is charged into the water phase. In such instances, the oil or water phase can be separately mixed or blended with the additives to produce a uniform phase prior to the mixing of the oil and water phase.

The aqueous phase is combined with the oil or wax, the surfactant, and the emulsifier, and mixed to produce a smooth and uniform cream or gel. Additional active agents are then added to the cream or gel. Various dermatologically acceptable acceptable fragrances and colorants may be added to the cream or gel. Deodorant or odor neutralizing agents such as Triclosan or Lemongrass derivative Citronellyl Methylcrotonate may also be added.

The preferred emulsion can be produced by the process comprising the following steps forming an aqueous phase under low shear conditions. In producing the stabilized emulsion of the preferred embodiment, the oil and water phases are formed either as a single phase process or separately. For example, in a first vessel, the water and water compatible agents are mixed together under low shear conditions at room temperature. The oil phase is introduced, preferably at a sufficient shear so that satisfactory dispersion of the oil phase can be achieved and the emulsion formed.

Example 1

In a first step of preparing a topical tanning cream, 0.4 parts by weight of Ultrez 10, a block copolymer of polyethylene glycol and a long chain alkyl acid ester, and 0.001 parts be weight of pantothenol (Provitamin $B_5$) are added to 62.3175 parts by weight of purified water. The resulting mixture is heated to 75-80° and blended until uniform. While maintaining the temperature, 3 parts by weight of a mixture of PEG-100 stearate and glyceryl stearate; 1 part of sorbitan stearate; 1 part of phenoxyethanol; 1 part of cetyl phosphate; and 0.0001 parts each of jojoba seed oil, olive oil, hemp seed oil, and carrot seed oil are individually added to the aqueous mixture. After mixing for 1 hour, temperature of the aqueous mixture is reduced to 65° C. and 17 parts by weight of a mixture of dimethicone and dimethicone crospolymer are added with mixing. After mixing for 2 hours, temperature is reduced to 60° C.

A silicone premix is then formed by combining 10 parts of cyclopentasiloxane, 0.01 parts retinyl palmitate, and 0.01 parts tocopheryl acetate. The silicone premix is added to the aqueous mixture at 60° C. and the resulting mixture is mixed for 1.5 hours to produce a uniform silicone-in-water emulsion. The temperature of the emulsion is reduced to 45° C., and 0.45 parts aminomethylpropanol are added with stirring for 1 hour; then the temperature of the composition is further reduced to 40° C.

Next, 0.0100 parts of a mixture of Calcium Ascorbate, Glycerin, and Sorbitol; 0.0001 parts of *Cimicifuga Racemosa* Root Extract; 0.0001 parts of Coenzyme Q10; 0.0001 parts Caffeine; 0.0001 parts White Birch Bark Extract; 0.0001 parts Milk Thistle Extract; 0.0001 parts of an *Aspalathus Linearis* (Rooibos) Leaf Extract in glycerin; 0.0001 parts White Tea Extract; 0.0001 parts of *Camellia Oleifera* (Japanese Green Tea) Leaf Extract in a Glycerin/Water mixture; 0.0001 parts α-lipoic acid; 0.1000 parts Triclosan; 0.2000 parts Citronellyl Methylcrotonate; 0.0001 parts of a liposomal preparation of Butylene Glycol, *Pyrus Malus* (Apple) Fruit Extract, Phospholipids, Tocopheryl Acetate, and Carbomer; 0.0001 parts *Punica Granatum* (Pomegranate) Extract in glycerin; and 1.0000 part Vanillyl Butyl Ether are added individually in the order listed to the silicone-in-water emulsion. The composition is mixed well after each addition.

Next, a premix composition containing tyrosine is prepared by mixing the following ingredients: melanin, acetyl tyrosine, methylsilanol acetyltyrosine, adenosine triphosphate, hydrolyzed vegetable protein, hydrolyzed citrus aurantium dulcis fruit extract, *musa sapientum* (banana) fruit extract, butylene glycol, water, and dextran. From 0.2 to 5 parts of the resulting tyrosine derivative-containing composition is added to the silicone-in-water emulsion with mixing. Next, 0.35 parts of a solution of 5% of glossy privet fruit extract in glycerin and 0.15 parts of a solution of *Hypericum Perforatum* flower, leaf and/or stem extracts in glycerin are added to the emulsion with low to moderate mixing. Colorants including a 1% solution of Yellow 5, a 1% solution of Red 40, and/or a 1% solution of Green 5 may be added to the emulsion with stirring. Spiced pumpkin may then be added in an amount of 1.5 parts as a fragrance. The composition is then cooled with continued mixing. The resulting composition is a smooth cream with a pH of 5.0-6.0.

Example 2

In a first step of making a tanning composition, 65. parts water are metered into a tank and heated to 75° C. to 80° C. Then 0.225 parts xanthan gum, 0.8 parts Ammonium Acryloyl Dimethyltaurate/Vinyl Pyrrolidone Copolymer; 0.1 parts panthenol; 1.5 parts glycerin; 1 part *Aloe Barbadensis* Leaf Juice; and 0.2 parts methylparaben are added to the water with mixing while maintaining the temperature to form an aqueous phase.

Next, the ingredients in Table 1 are individually added to the aqueous phase, while allowing each solid ingredient to be fully incorporated into the solution before adding the next ingredient.

TABLE 1

| Parts by weight | Ingredient |
| --- | --- |
| 2.0000 | Cetearyl Alcohol and Ceteareth-20 |
| 0.5000 | Sorbitan Stearate |
| 1.0000 | Myristyl Myristate |
| 1.5000 | *Prunus Amygdalus Dulcis* (Sweet Almond) Oil |
| 0.0100 | *Corylus Avellana* (Hazel) Seed Oil |
| 0.0120 | *Borago Officinalis* (Borage) Seed Oil |
| 0.5000 | *Aleurites Moluccana* (Kukui) Seed Oil |
| 0.0001 | *Cannabis Sativa* (Hemp) Seed Oil |
| 0.0001 | *Vitis Vinifera* (Grape) Seed Oil |
| 4.0000 | Caprylic/Capric Triglyceride |
| 2.0000 | C12-15 Alkyl Benzoate |
| 1.5000 | PEG-7 Glyceryl Cocoate |
| 0.5000 | Biosaccharide Gum-1 |
| 0.2000 | Triclosan |
| 0.1000 | Propylparaben |

After the ingredients in Table 1 are added, the batch is mixed while maintaining temperature for 30 minutes. The mixture is then cooled to 35° C. with mixing. At this point, 3 parts of Sepigel 305, a thickener composition containing a mixture of 1.4 parts of a polyacrylamide thickener, 0.875 parts of a C13-C14 isoparaffin, and less than 1 part of a PEG-7 lauryl ether nonionic surfactant, are combined with 2 parts of dimethicone and added to the aqueous phase with mixing. The batch thickens upon addition of the polyacrylamide component. The composition is cooled to between 40 and 42° C. with continued mixing to form an emulsion.

At this point, the ingredients in Table 2 are individually added to the aqueous phase with mixing.

TABLE 2

| Parts by weight | Ingredient | Components within ingredient |
| --- | --- | --- |
| 0.4000 | Germall 2 | Diazolidinyl Urea |
| 0.0001 | Caffeine | Caffeine |
| 0.0001 | Milk Thistle Extract | *Silybum Marianum* (Milk Thistle) Extract, water |
| 0.0001 | White Tea Extract | *Camellia Sinensis* (White Tea) Leaf Extract |
| 0.0001 | Firming Liposome Complex | Water, Butylene Glycol, *Pyrus Malus* (Apple) Fruit Extract, Phospholipids, Tocopheryl Acetate, Carbomer |
| 0.0001 | Nano-Lipobelle DN Q10 Mibelle/TRI-K) | Lecithin, Ubiquinone (Coenzyme Q10), Ascorbyl Tetraisopalmitate, Tocopherol, Vegetable Oil, Glycerin, Water, Benzoic Acid |
| 0.0001 | AC Essential Fatty Acid Complex | Omega-6 Linoleic Acid, Omega-3 Linolenic Acid, Tocopherol |
| 0.0001 | Grape Seed Extract | *Vitis Vinifera* (Grape) Seed Extract (Resveratrol) |
| 0.0001 | Ascorbic Acid (Vitamin C) | Ascorbic Acid (Vitamin C) |
| 0.0001 | Actiphyte of Yam GL | Glycerin, Water, Dioscorea Villosa (Wild Yam) Root Extract |
| 0.0001 | Phytessence French Rose | Water, Butylene Glycol, *Rosa Gallica* (French Rose) Flower Extract |
| 0.2500 | Optivegitol | Wine Extract |
| 0.2500 | Advanced Moisture Complex R10417 | Glycerin, Water, Sodium PCA, Urea, Trehalose, Polyquaternium-51, Sodium Hyaluronate (Advanced Moisture Complex ™) |
| 1.5000 | Witch Hazel Extract | *Hamamelis Virginiana* (Witch Hazel) Bark/Leaf/Twig Extract |
| 0.0001 | Actiphyte of Rooibos | *Aspalathus Linearis* (Rooibos) Leaf Extract, Water, Glycerin |
| 0.0001 | ACB OX RED SOD | Superoxide Dismutase |
| 0.0001 | Alpha Lipoic Acid | Thioctic (Alpha Lipoic) Acid |
| 2.0000 | Cyclomethicone | Cyclopentasiloxane |

Next, 0.1 parts of a tyrosine-based composition containing butylene glycol, acetyl tyrosine, hydrolyzed vegetable protein, and adenosine triphosphate is prepared. To this composition, 0.2 parts methylsilanol acetyltyrosine; 0.1 parts melanin; 0.1 parts of an aqueous glycerin solution of *Musa Sapientum* (banana) fruit extract, and 0.1 parts of Hydrolyzed Citrus Aurantium Dulcis Fruit Extract are added. Finally, 0.05 parts Potassium Caproyl Tyrosine, 0.25 parts of the bronzer *Juglans Nigra* (Black Walnut) Leaf Extract, and 0.2 parts erythrulose are added to the tyrosine-based composition. The tyrosine-based composition is then added to the emulsion.

A warming composition is now prepared by combining the ingredients in Table 3. This warming composition includes various plant extracts, vanillyl butyl ether, and arginine. The warming composition is added to the emulsion with stirring.

TABLE 3

| Parts by weight | Ingredient |
| --- | --- |
| 1.0000 | Dimethyl Isosorbide |
| 0.5000 | Water, *Zingiber Officinale* (Ginger) Root Extract |
| 0.0500 | Arginine |
| 0.5000 | Glycerin, Water, *Cinnamomum Zeylanicum* Bark Extract |
| 0.5000 | *Myrica Cerifera* (Bayberry) Fruit Extract, Water |
| 0.5000 | Glycerin, Water, *Citrus Aurantium Bergamia* (Bergamot) Leaf Extract |
| 0.3500 | Vanillyl Butyl Ether |

Next, 0.7 parts of a solution of 5% of glossy privet fruit extract in glycerin, 0.35 parts of Phellodendron Amurense Bark Extract in aqueous glycerin, and 0.3 parts of a solution of *Hypericum Perforatum* flower, leaf and/or stem extracts in glycerin are added to the emulsion with low to moderate mixing. Colorants including 0.45 parts of a 1% solution of Yellow 5, 0.43 parts of a 1% solution of Red 40, and/or 0.28 parts of a 1% solution of Green 5 may be added to the emulsion with stirring. Tropical papaya guava may then be added in an amount of 1.9 parts as a fragrance. The composition is then cooled with continued mixing. The resulting composition is a thick lotion with a pH of 4.5 to 5.5.

Example 3

A warming lotion is prepared by mixing, in a first vessel, 10 parts of Dow Corning 3225C Formulation Aid, which is a dispersion of a polyethylene glycol/polypropyleneglycol/silicone surfactant copolymer in cyclomethicone; 17 parts of Cyclopentasiloxane, Cyclohexasiloxane, dimethicone, or a mixture thereof; and 1 part vanillyl butyl ether. In a second vessel, 58.7 parts water, 13 parts glycerin, 0.2 parts polysorbate 80, 1 part sodium chloride, and 0.1 parts of the preservative Quaternium-15 (N-(3-chloroallyl) hexaminium chloride) are combined to form an aqueous phase and mixed to form a clear solution. The aqueous phase is added to the silicone phase in the first vessel, and the resulting mixture is stirred until a thick and uniform emulsion is formed.

Example 4

A warming body balm is prepared. In a first step, 3 parts of Sepigel 305, a thickener composition containing a mixture of 1.4 parts of a polyacrylamide thickener, 0.875 parts of a C13-C14 isoparaffin, and less than 1 part of a PEG-7 lauryl ether nonionic surfactant, are combined with 7 parts of Dow Corning 9040, a mixture of cyclomethicone and dimethicone crospolymer in a first tank and mixed to prepare a smooth and uniform gel. In a second tank, 67.15 parts water are mixed with 2 parts *Aloe Barbadensis* Leaf Juice; 1 part white nettle extract; 1 part of a ginger extract, 3 parts ethoxydiglycol; 0.25 parts L-arginine; 1 part cinnamon extract; 0.5 parts of a capsicum extract; 1 part aqueous bayberry fruit extract; 1 part bergamot extract; 1 part Hawaiian White Ginger extract; and 0.5 parts polysorbate 20. The aqueous mixture in the second tank is then added to the silicone mixture in the first tank with constant stirring.

Next, 0.2 parts of a tyrosine-based premix containing butylene glycol, acetyl tyrosine, hydrolyzed vegetable protein, and adenosine triphosphate is prepared. To this composition, 0.2 parts methylsilanol acetyltyrosine; 0.1 parts melanin; 0.1 parts of an aqueous glycerin solution of *Musa Sapientum* (banana) fruit extract, and 0.2 parts of Hydrolyzed Citrus Aurantium Dulcis Fruit Extract are added. The premix is heated to 40° C. and slowly added to the first tank with constant stirring.

Next, 0.7 parts of a solution of 5% of glossy privet fruit extract in glycerin and 0.3 parts of a solution of *Hypericum Perforatum* flower, leaf and/or stem extracts in aqueous glycerin are combined and added to the emulsion with low to moderate mixing. Then 0.1 parts each of retinyl palmitate, a form of vitamin A, and tocopheryl acetate, a Vitamin E derivative, and calcium ascorbate are added to the emulsion with constant stirring.

A warming composition is then prepared by mixing 1 part vanillyl butyl ether, 3 parts hydrogenated polydecene, and 7 parts neopentyl glycol dicaprylate. This warming composition is then slowly added to the emulsion with constant mixing. Phenoxyethanol is then added to the composition in an amount of 1 part by weight. Honey pear may then be added in an amount of 1.6 parts as a fragrance. The composition is then ready for use as a tanning lotion.

What is claimed is:

1. A topical composition comprising:
   a) a vehicle, said vehicle including an emulsion or dispersion of water in an amount of from 50% by weight to 93% by weight; and a non-aqueous discontinuous phase in an amount of from 50% by weight to 7% by weight;
   b) at least one of a bronzer and at least one of a tanning accelerator selected from the group consisting of i) tyrosine, a tyrosine derivative, or a mixture thereof; ii) α-melanocyte stimulating hormone, β-melanocyte stimulating hormone, γ-melanocyte stimulating hormone, or analogs thereof; or iii) a combination of (i) and (ii); and
   c) from 0.01% by weight to 5% by weight of a warming agent, based on the total weight of the composition;
   said warming agent comprising at least one alkyl ether of vanillyl alcohol or at least one N-alkyl amide of vanillic acid;
   wherein said warming agent is present in an amount effective to produce a prolonged warming sensation when applied to a user's skin;
   wherein said bronzer is selected from the group consisting of black walnut extract, henna extract, kukui nut husk extract, and gymnema extract, and mixture thereof;
   wherein said composition is transparent to UV radiation; and
   wherein said composition does not include zinc.

2. A topical composition comprising:
   a) a vehicle, said vehicle including an emulsion or dispersion of water in an amount of from 50% by weight to 93% by weight; and a non-aqueous discontinuous phase in an amount of from 7% by weight to 50% by weight;
   b) a bronzer;
   c) a tanning accelerator selected from the group consisting of:
      i) tyrosine, a tyrosine derivative, or a mixture thereof;
      ii) α-melanocyte stimulating hormone, β-melanocyte stimulating hormone, γ-melanocyte stimulating hormone, and analogs thereof; or
      iii) a combination of (i) and (ii); and
   d) from 0.01% by weight to 5% by weight of a warming agent, based on the total weight of the composition;
   said warming agent comprising at least one alkyl ether of vanillyl alcohol or at least one N-alkyl amide of vanillic acid;
   wherein said warming agent is present in an amount effective to produce a prolonged warming sensation when applied to a user's skin;
   wherein said composition is transparent to UV radiation; and
   wherein said bronzer is selected from the group consisting of black walnut extract, henna extract, kukui nut husk extract, gymnema extract, and mixtures thereof.

3. A topical composition according to claim 1, wherein the nonaqueous phase comprises at least one material selected from the group consisting of a cyclic or acyclic silicone oil, a wax or oil selected from the group consisting of peanut oil, soya bean oil, sunflower oil, sesame oil, coconut oil, olive oil, C12-C26 fatty alcohols, C12-C26 fatty acids, alkyl esters of C12-C26 fatty acids, C2-C5 linear or branched glycol diesters of C12-C26 fatty acids, C12-C26 fatty alcohol esters of carboxylic acids, beeswax, carnauba wax paraffin wax, and mixtures thereof.

4. A topical composition according to claim 1, wherein the composition further comprises an anionic surfactant, a cationic surfactant, a nonionic surfactant, a zwitterionic surfactant, or a mixture of a nonionic surfactant with a cationic surfactant or a nonionic surfactant.

5. A topical composition according to claim 1, wherein the composition further comprises at least one thickener selected from the group consisting of polysaccharide starches; vegetable gums; albumin; gelatin; hydrolyzed vegetable protein; collagen; polyacrylate thickeners; polyacrylamide thickeners; sorbitol; xylitol; dextran; maltitol; polydextrose; and quillaia.

6. A method of indoor tanning, comprising:
   A) a step of applying the topical composition in claim 1 to an exposed skin surface; and
   B) a step of exposing the exposed skin surface to an indoor source of ultraviolet light.

7. A method of indoor tanning according to claim 6, wherein the nonaqueous phase comprises at least one material selected from the group consisting of a cyclic or acyclic silicone oil, a wax or oil selected from the group consisting of peanut oil, soya bean oil, sunflower oil, sesame oil, coconut oil, olive oil, C12-C26 fatty alcohols, C12-C26 fatty acids, alkyl esters of C12-C26 fatty acids, C2-C5 linear or branched glycol diesters of C12-C26 fatty acids, C12-C26 fatty alcohol esters of carboxylic acids, beeswax; carnauba wax; paraffin wax, and mixtures thereof.

8. A method of indoor tanning according to claim 6, wherein the composition further comprises an anionic surfactant, a cationic surfactant, a nonionic surfactant, a zwitterionic surfactant, or a mixture of a nonionic surfactant with a cationic surfactant or a nonionic surfactant.

9. A method of indoor tanning according to claim 6, wherein the composition further comprises at least one thickener selected from the group consisting of polysaccharide starches; vegetable gums; albumin; gelatin; hydrolyzed vegetable protein; collagen; polyacrylate thickeners; polyacrylamide thickeners; sorbitol; xylitol; dextran; maltitol; polydextrose; and quillaia.

10. A topical composition according to claim 2, wherein the nonaqueous phase comprises at least one material selected from the group consisting of a cyclic or acyclic silicone oil, a wax or oil selected from the group consisting of peanut oil, soya bean oil, sunflower oil, sesame oil, coconut oil, olive oil, C12-C26 fatty alcohols, C12-C26 fatty acids, alkyl esters of C12-C26 fatty acids, C2-C5 linear or branched glycol diesters of C12-C26 fatty acids, C12-C26 fatty alcohol esters of carboxylic acids, beeswax, carnauba wax, paraffin wax, and mixtures thereof.

11. A topical composition according to claim 2, wherein the composition further comprises an anionic surfactant, a cationic surfactant, a nonionic surfactant, a zwitterionic surfactant, or a mixture of a nonionic surfactant with a cationic surfactant or a nonionic surfactant.

12. A topical composition according to claim 2, wherein the composition further comprises at least one thickener selected from the group consisting of polysaccharide starches, vegetable gums, albumin, gelatin, hydrolyzed vegetable protein, collagen, polyacrylate thickeners, polyacrylamide thickeners, sorbitol, xylitol, dextran, maltitol, polydextrose, and quillaia.

13. A topical composition consisting of:
a) a vehicle, said vehicle including an emulsion or dispersion of water in an amount of from 50% by weight to 93% by weight; and a non-aqueous discontinuous phase in an amount of from 7% by weight to 50% by weight;
b) a bronzer;
c) a tanning accelerator selected from the group consisting of:
  i) tyrosine, a tyrosine derivative, or a mixture thereof;
  ii) α-melanocyte stimulating hormone, β-melanocyte stimulating hormone, γ-melanocyte stimulating hormone, and analogs thereof; or
  iii) a combination of (i) and (ii); and
d) from 0.01% by weight to 5% by weight of a warming agent, based on the total weight of the composition;
  said warming agent comprising at least one alkyl ether of vanillyl alcohol or at least one N-alkyl amide of vanillic acid;
  wherein said warming agent is present in an amount effective to produce a prolonged warming sensation when applied to a user's skin; and
  wherein said bronzer is selected from the group consisting of black walnut extract, henna extract, kukui nut husk extract, and gymnema extract.

14. A topical composition consisting of:
a) a vehicle, said vehicle including an emulsion or dispersion of water in an amount of from 50% by weight to 93% by weight; and a non-aqueous discontinuous phase in an amount of from 50% by weight to 7% by weight;
b) at least one of a bronzer and at least one of a tanning accelerator selected from the group consisting of i) tyrosine, a tyrosine derivative, or a mixture thereof; ii) α-melanocyte stimulating hormone, β-melanocyte stimulating hormone, γ-melanocyte stimulating hormone, or analogs thereof; or iii) a combination of (i) and (ii); and
c) from 0.01% by weight to 5% by weight of a warming agent, based on the total weight of the composition;
d) an optional thickener; and
e) an optional surfactant;
  said warming agent comprising at least one alkyl ether of vanillyl alcohol or at least one N-alkyl amide of vanillic acid;
  wherein said warming agent is present in an amount effective to produce a prolonged warming sensation when applied to a user's skin;
  wherein said bronzer is selected from the group consisting of black walnut extract, henna extract, kukui nut husk extract, and gymnema extract, and mixture thereof;
  wherein said composition is transparent to UV radiation; and
  wherein said composition does not include zinc.

* * * * *